United States Patent [19]

Nishibayashi et al.

[11] Patent Number: 4,709,090
[45] Date of Patent: Nov. 24, 1987

[54] METHOD OF PRODUCTION OF OXYDICARBOXYLIC ACID SALTS

[75] Inventors: Hideyuki Nishibayashi, Machida; Shigeyoshi Iio, Yokohama; Fumio Watanabe, Kawasaki; Takakiyo Goto, Yokohama, all of Japan

[73] Assignee: Nippon Shokubai Kagaku Kogyo Co., Ltd., Osaka, Japan

[21] Appl. No.: 843,863

[22] Filed: Mar. 24, 1986

Related U.S. Application Data

[63] Continuation of Ser. No. 701,622, Feb. 14, 1985.

[30] Foreign Application Priority Data

Sep. 7, 1984 [JP] Japan ............................... 59-186577

[51] Int. Cl.[4] .......................................... C07C 51/295
[52] U.S. Cl. .................................. 562/537; 562/539; 502/345
[58] Field of Search .................. 562/537, 539; 502/345

[56] References Cited

U.S. PATENT DOCUMENTS

| | | | |
|---|---|---|---|
| 2,183,853 | 12/1939 | Mannheim et al. | 562/539 |
| 2,384,817 | 9/1945 | Chitwood | 562/537 |
| 2,688,603 | 9/1954 | Baldwin | 502/345 |
| 2,886,590 | 5/1959 | Montgomery et al. | 562/539 |
| 3,717,676 | 2/1973 | Bechara et al. | 562/539 |
| 3,862,055 | 1/1975 | Eurlings et al. | 502/345 |
| 3,929,873 | 12/1975 | Gammans | 562/539 |
| 4,110,371 | 8/1978 | Schulze et al. | 562/537 |
| 4,459,372 | 7/1984 | Arena | 502/345 |

FOREIGN PATENT DOCUMENTS 59-87044  5/1984  Japan ................................ 502/345

OTHER PUBLICATIONS

Yoneoka et al., *Chemical Abstracts*, vol. 93, No. 204080f, (1980).

*Primary Examiner*—Howard T. Mars
*Assistant Examiner*—Bruce D. Gray
*Attorney, Agent, or Firm*—Omri M. Behr

[57] ABSTRACT

A method for the manufacture of an oxydicarboxylic acid salt which comprises subjecting to dehydrogenation an polyethylene glycol represented by the general formula I:

$$HO\text{---}(CH_2CH_2O)_n\text{H} \quad (I)$$

wherein n is 2 to 14, in the presence of the hydroxide of at least one metal selected from the group consisting of alkali metals and alkaline earth meatals, water and a catalyst containing copper and zirconium compound.

16 Claims, No Drawings

METHOD OF PRODUCTION OF OXYDICARBOXYLIC ACID SALTS

This application is a continuation of application Ser. No. 701,622, filed 2/14/85.

BACKGROUND OF THE INVENTION

1. Field of the Invention

This invention relates to a method for the production of oxydicarboxylic acid salts. More particularly, this invention relates to a method for the production of an oxydicarboxylic acid salt by the liquidphase dehydrogenation of corresponding polyethylene glycols possessing 2 to 14 oxyethylene units.

2. Description of Prior Art

Oxydicarboxylic acid salts excel in chelating ability and exhibit satisfactory biodegradability and, therefore, are accepted as useful compounds for builders in synthetic detergents. Particularly in recent years, they have come to attract keen attention because tripolyphosphates have been held responsible for eutrophication of rivers, brooks, lakes and swamps, and the existing builders for detergents have been moving toward substitution with new substances. Besides excelling in chelating ability and biodegradability, oxydicarboxylic acid salts exhibit high compatibility with surface active agents and possess outstanding properties befitting builders for detergents. This fact is directing growing interest to use such oxydicarboxylic acid salts either independently or in combination with builders such as zeolite.

As means of producing oxydicarboxylic acids, it is known to oxidize polyethylene glycols to corresponding oxydicarboxylic acids with nitric acid, and with a gas containing molecular oxygen in the presence of a catalyst of noble metal such as palladium (U.S. Pat. No. 3,929,873), and to dehydrogenate in the presence of a caustic alkali. The method which produces oxydicarboxylic acid salts by the oxidation of polyethylene glycols with nitric acid requires use of nitric acid of high concentration and, moreover, entails the problem of corrosion of the equipment used for the oxidation and suffers from the disadvantage that oxydicarboxylic acid salts produced by the oxidation are difficult of separation and purification. In the case of the method which oxidizes by the use of a noble metal such as platinum or palladium, the disadvantage that the catalyst is expensive and, consequently, the production cost is high and the difficulty of separation of aldehyde which is formed by oxidation have posed itself a serious problem on the way of commercialization of this method.

The method which produces oxydicarboxylic acid salts by liquid-phase dehydrogenation of alcohols in a caustic alkali in the absence of a catalyst has the disadvantage that since the reaction proceeds only at an elevated temperature in the neighborhood of 300° C., alcohols such as polyethylene glycols which have ether bonds in the molecular units thereof under such reaction conditions by-produce glycolates, acetates, and oxalates in large amount and produce oxydicarboxylic acid salts in low yields because of cleavage of the ether bonds.

U.S. Pat. No. 2,384,817 discloses a method for the production of carboxylates by the dehydrogenation of alcohols such as, for example, ethanol, propanol, ethylene glycol, polyethylene glycol and momoethanol amine in the presence of a caustic alkali, which method permits use of a metal such as cadmium, copper, nickel, silver, lead or zinc or a compound of such a metal as the catalyst for the reaction. Further, U.S. Pat. No. 2,384,817 contains statements indicating that in the catalysts mentioned above, cadmium and compounds thereof exhibit the best effects, that copper compounds exhibit high initial activity but the duration of maximum catalytic activity is short, and that the other catalysts, i.e. nickel, silver, lead and zinc compounds exhibit notably lower levels of activity than copper and cadmium compounds.

U.S. Pat. No. 3,717,676 limits the alcohols set forth in the aforementioned U.S. Pat. No. 2,384,817 to only polyethylene glycols and lays down the requirement that the reaction should be carried out in the presence of a cadmium catalyst. The fact that this method uses cadmium as a catalyst, however, poses itself a problem on the way to commercialization of this method.

Japanese Patent Publication No. SHO 57(1982)-5,775 discloses a method which, by use of a catalyst containing copper and/or nickel, produces disodium oxydiacetate in high yields. When the reaction proceeds in the presence of nickel or a nickel-containing compound is used as catalyst, oxalates and carbonates occur in large amounts because of cleavage of ether bonds and, consequently, disodium oxydiacetate is produced in low yields. An attempt to obtain disodium oxydiacetate of high purity from the resultant reaction mixtures, therefore, necessitates a complicate process for purification. On the other hand, the catalyst formed solely of copper which exhibits high activity at an elevated reaction temperature suffers from serious loss of catalytic activity and withstands only one of two cycles of reaction. When the reaction temperature is lowered for the purpose of elongating the service life is the catalyst, the reaction velocity is lowered too much for the reaction itself to be practicable.

U.S. Pat. No. 4,110,371 discloses a method for the production of oxydicarboxylic acid salts by the reaction of corresponding polyethylene glycols at elevated temperatures in the presence of a nickel-copper-chromia catalyst. This method, however, produces oxydicarboxylic acid salts in low yields.

An object of this invention, therefore, is to provide a novel method for the production of an oxydicarboxylic acid salt.

Another object of this invention is to provide a method for the production of an oxydicarboxylic acid salt by the liquid-phase dehydrogenation of polyethylene glycols having 2 to 14 oxyethylene units.

SUMMARY OF THE INVENTION

The objects described above are accomplished by a method for the production of an oxydicarboxylic acid salt by the reaction of a polyethylene glycol represented by the general formula I:

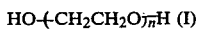

$$HO{-}(CH_2CH_2O)_{\overline{n}}H \quad (I)$$

wherein n denotes a value of 2 to 14, in the presence of a hydroxide of a least one metal selected from the group consisting of alkali metals and alkaline earth metals, water and catalyst containing copper and zirconium compound.

In accordance with this invention, the use of the aforementioned catalyst enables the desired oxydicarboxylic acid salt to be produced in an improved yield, permits a decrease in the reaction time, allows the reaction to proceed under mild conditions, and warrants repeated use of the catalyst itself in successive cycles of reaction as compared with the conventional method. As the result, this invention ensures an ample reduction in the production cost and promises easy commercialization of the production of oxydicarboxylic acid salts from polyethylene glycols possessing 2 to 14 oxyethylene units.

EXPLANATION OF PREFERRED EMBODIMENTS

In accordance with this invention, a polyethylene glycol represented by the aforementioned general formula I is dehydrogenated in the presence of a hydroxide of at least one metal selected from the group consisting of alkali metals and alkaline earth metals, water and a catalyst containing copper and zirconium compound. This reaction produces a corresponding oxydicarboxylic acid salt.

In the aforementioned general formula I, the symbol n denotes a value of 2 to 14. When the value of n is in the range of 2 to 5, it turns out to be substantially an integer because the corresponding polyethylene glycol can be isolated in high concentration. When the value of n exceeds 6, since the corresponding polyethylene glycol is generally obtained in the form of a mixture, the value turns out to be what is calculated by averaging the molecular weights of the component compounds of the mixute.

Typical polyethylene glycols include diethylene glycol, triethylene glycol, tetraethylene glycol, pentaethylene glycol and polyethylene glycols having average molecular weights in the range of 200, 300 and 400.

In the catalyst of this invention which contains copper and zirconium compound, the copper is used in the form of copper as elemental metal or metal compound. The zirconium is used as of zirconium compound. As starting materials, inorganic salts such as nitrates, sulfates, carbonates, oxides, halides and hydroxides, and organic salts such as acetates, oxalates, citrates and lactates can be cited. Particularly, such salts of high water-solubility prove advantageous. The catalyst is not particularly defined by its form. A catalyst containing copper and zirconium compound which is obtained by dissolving a copper compound and a zirconium compound in water, adding an aqueous alkali solution to the resultant solution thereby inducing precipitation of a hydroxide, washing the precipitate with water, drying the washed precipitate, calcining the dried precipitate, and thereafter subjecting the calcined precipitate to reduction in an atmosphere of hydrogen proves advantageous. Another catalyst having copper deposited on zirconium oxide which is obtained by impregnating zirconium oxide with an aqueous copper compound solution, drying the wet zircnium compound composite, calcining this composite, and thereafter subjecting the resultant calcined product to reduction in an atmosphere of hydrogen also proves advantageous. Typical zirconium compounds available for preparation in the catalyst are zirconium oxynitrate, zirconium nitrate, zirconium oxysulfate, zirconium sulfate, zirconium oxycarbonate, zirconium carbonate, zirconium oxide, zirconium oxychloride, zirconium tetrachloride, zirconium hydroxide, zirconium oxyacetate, zirconium acetate and zirconium oxalate.

In the catalyst containing copper and a zirconium compound, the composition of the copper and the zirconium compound is such that the proportion of the zirconium to the copper taken as 1 is in the range of 40 to 1, preferably 20 to 2, by weight.

The amount of the catalyst to be used in the reaction is in the range of 1 to 70% by weight, preferably 5 to 30% by weight, based on the polyethylene glycol.

Since this catalyst generally undergoes only low deterioration of activity due to reaction, it can be used repeatedly in successive cycles of reaction. Optionally, this catalyst may be used on the one-pass basis.

In the reaction of the present invention, water is indispensable for the purpose of increasing the reaction velocity and obtaining the oxydicarboxylic acid salt in a high yield. The amount of this water to be used in the reaction is required to exceed 10% by weight and desired to fall in the range of 25 to 500% by weight, based on the aforementioned polyethylene glycol.

Typical examples of the hydroxide of at least one member selected from the group consisting of alkali metals are lithium hydroxide, sodium hydroxide, potassium hydroxide, rubidium hydroxide and cesium hydroxide. Typical examples of the hydroxide of an alkaline earth metal are magnesium hydroxide, calcium hydroxide, and barium hydroxide. In all these hydroxides, hydroxides of alkali metals and particularly sodium hydroxide and/or potassium hydroxide are used advantageously. The amount of the hydroxide of at least one metal selected from the group consisting of alkali metals and alkaline earth metals to be used is in the range of 0.8 to 1.5, preferably 0.9 to 1.2 equivalent relative to the hydroxyl group of the aforementioned polyethylene glycol being used in the reaction. The hydroxide of at least one metal selected from the group consisting of alkali metals and alkaline earth metals can be used in the form of flakes, powder, pellets or an aqueous solution. Generally, it is used advantageously in the form of aqueous solution because of the convenience of handling.

The reaction temperature is required to be not more than 250° C. for the purpose of preventing the ether bond of the polyethylene glycol and that of the oxydicarboxylic acid salt from undergoing thermal decomposition or hydrogenolysis. Generally, the reaction is carried out at temperatures in the range of 120° to 250° C., preferably 150° to 220° C. The catalyst containing copper and zirconium compound, when the reaction temperature exceeds 250° C., begins to entail the phenomenon that part of the surface thereof is sintered and the catalyst suffers from loss of activity owing to the decrease in the surface area. In the case of repeated use of the catalyst, therefore, the reaction temperature is desired to be not more than 250° C.

Since the reaction is hydrogenation, the reaction pressure is desired to be as low as permissible for the standpoint of the reaction velocity. Generally it is required to exceed the minimum pressure at which the reaction proceeds in the liquid phase. It is desired to fall in the range of 0 to 50 kg/cm$^2$.G, preferably 5 to 30 kg/cm$^2$.G.

This invention, which is directed to the production of oxydicarboxylic acid salt from corresponding polyethylene glycol, is characterized in that the yield of the oxydicarboxylic acid salt is heightened up to the level of 90 to 95 mol% based on the polyethylene glycol by the use of a catalyst containing copper and zirconium compound and having no possibility of inducing the problem of environmental pollution and that the catalyst is enabled to be used repetitively over a long period in successive cycles of reaction.

Even when the reaction is carried out in the presence of copper alone such as, Raney-copper, the oxydicarboxylic acid salt can be obtained in a high yield. The catalyst containing copper and zirconium compound has a decisively longer service life than copper used alone. It further excels in selectivity and activity and, therefore, enables the reaction to proceed under mild conditions. As the result, the reaction product entrains by-products in extremely small amounts. Thus, the reaction product can be converted into a finished product simply by the removal of the catalyst. The catalyst which has high activity and high selectivity and enjoys a long service life as described above is obtained only by combining copper and a zirconium compound.

The oxydicarboxylic acid salt so produced has originated in a corresponding polyethylene glycol. Examples of the oxydicarboxylic acid salt are those which correspond to diethylene glycol, triethylene glycol, tetraethylene glycol, pentaethylene glycol and polyethylene glycol having average molecular weights of 200, 300 and 400.

The reaction may be carried out either batchwise or continuously.

Now, this invention will be described more specifically below with referance to working examples. It should be noted, however, that this invention is not limited to these working examples.

The numerical values of the conversion of polyethyleneglycol and the selectivity to oxidicarboxylic acid salt indicated in the following working examples are results of calculation based on the following formulas.

Conversion of polyethylene glycol (%) =

$$\frac{\text{Number of mols of reacted polyethylene glycol}}{\text{Number of mols of fed polyethylene glycol}} \times 100$$

Selectivity to oxydicarboxylic acid salt (%) =

$$\frac{\text{Number of mols of formed oxidicarboxylic acid salt}}{\text{Number of mols of reacted polyethylene glycol}} \times 100$$

EXAMPLE 1

An autoclave having an inner volume of 500 ml was charged with 84.8 g (0.80 mol) of diethylene glycol, 70.4 g (1.76 mol) of sodium hydroxide, 161 g of water and 8.5 g of a catalyst containing copper and zirconium compound which had been obtained by adding to a solution of 24.8 g of zirconium oxychloride and 4.0 g of copper nitrate in 300 ml of water an aqueous sodium hydroxide solution to cause precipitation of hydroxide, washing the precipitate with water, drying it, heating the dry precipitate in air at 500° C. for 3 hours, and subjecting the resultant composite to reduction under a current of hydrogen gas at 230° C. for 6 hours. After the interior of the autoclave had been displaced with hydrogen gas three times, the reaction was continued at a temperature of 180° C. under a pressure of 10 kg/cm$^2$.G until generation of hydrogen ceased. The time required for the reaction was 5 hours after the temperature had reached 180° C. After completion of the reaction, the reaction product was sampled and analyzed. By the analysis, the conversion of diethylene glycol was found to be 99.8 mol% and the selectivity to disodium oxydiacetate to be 95.5 mol%.

EXAMPLE 2

An autoclave having an inner volume of 500 ml was charged with 84.8 g (0.80 mol) of diethylene glycol, 70.4 g (1.76 mol) of sodium hydroxide, 161 g of water and 8.5 g of a catalyst having copper deposited on zirconium oxide which had been obtained by impregnating 10 g of zirconium oxide with an aqueous solution containing 4.2 g of copper nitrate, drying the wet composite, heating the dried composite in air at 500° C. for 3 hours, and subjecting the oxidized composite to reduction under a current of hydrogen gas at 230° C. for 6 hours. After the interior of the autoclave had been displaced with hydrogen gas three times, the reaction was continued at a temperature of 180° C. under a pressure of 10 kg/cm$^2$.G until generation of hydrogen ceased. The time required for the reaction was 5 hours after the temperature had reached 180° C. After completion of the reaction, the reaction product was sampled and analyzed. By the analysis, the conversion of diethylene glycol was found to be 99.6 mol% and the selectivity to disodium oxydiacetate to be 95.1 mol%.

EXAMPLE 3

To test the catalyst of Example 1 for activity in repeated use, the reaction of Example 1 was performed recurrently under the same conditions. The time required for the reaction in the 10th cycle was 8 hours after the temperature had reached 180° C. After completion of the reaction, the reaction product was sampled and analyzed. By the analysis, the conversion of diethylene glycol was found to be 99.8 mol% and the selectivity to disodium oxydiacetate to be 94.1 mol%.

Control 1:

An autoclave having an inner volume of 500 ml was charged with 84.8 g (0.80 mol) of diethylene glycol, 70.4 g (1.76 mol) of sodium hydroxide, 161 g of water and 8.5 g of developed Raney nickel. After the interior of the autoclave had been displaced with hydrogen gas three times, the reaction was continued at a temperature of 170° C. under a pressure of 10 kg/cm$^2$.G until generation of hydrogen ceased. The time required for the reaction was 4 hours after the temperature had reached 170° C. After completion of the reaction, the reaction product was sampled and analyzed. By the analysis, the conversion of diethylene glycol was found to be 98.6 mol% and the selectivity to disodium oxydiacetate to be 63 mol%. Selectively of sodium oxalate, sodium acetate and sodium carbonate which are decomposition products are respectively 1.5 mol%, 7.1 mol% and 7.6 mol%.

Control 2:

An autoclave having an inner volume of 500 ml was charged with 84.8 g (0.80 mol) of diethylene glycol, 70.4 g (1.76 mol) of sodium hydroxide, 161 g of water and 8.5 g of developed Raney copper. After the interior of the autoclave had been displaced with hydrogen gas three times, the reaction was continued at a temperature of 200° C. under a pressure of 10 kg/m$^2$.G until generation of hydrogen ceased. The time required for the reaction was 5 hours after the temperature had reached 200° C. After completion of the reaction, the reaction product was sampled and analyzed. By the analysis, the conversion of diethylene glycol was found to be 99.6 mol% and the selectivity to diglycolic acid salt to be 93.2 mol%.

Control 3:

To test the Raney copper catalyst for activity in repeated use, the reaction of Control 2 was performed recurrently under the same conditions. The time required for the reaction in the 3th cycle was 15 hours after the temperature had elevated. After completion of the reaction, the reaction product was sampled and analyzed. By the analysis, the conversion of diethylene glycol was found to be 98.6 mol% and the selectivity of disodium oxydiacetate to be 79.5 mol%.

EXAMPLE 4

An autoclave having an inner volume of 500 ml was charged with 90.1 g (0.60 ml) of triethylene glycol, 48.0 g (1.20 mol) of sodium hydroxide, 138 g of water and 9.0 g of a catalyst containing copper and zirconium compound which had been obtained by adding to a solution of 20.6 g of zirconium oxychloride and 4.0 g of copper nitrate in 300 ml of water an aqueous sodium hydroxide solution to cause precipiration of hydroxide, washing the precipitate with water, drying it, heating dry precipitate in air at 500° C. for 3 hours, and subjecting the resultant composite to reduction under a current of hydrogen gas at 230° C. for 6 hours. After the interior of the autoclave had been displaced with hydrogen gas three times, the reaction was continued at a temperature of 180° C. under a pressure of 10 kg/cm$^2$.G until generation of hydrogen ceased. The time required for the reaction was 6.5 hours after the temperature had reached 180° C. After completion of the reaction, the reaction product was sampled and analyzed. By the analysis, the conversion of triethylene glycol was found to be 99.2 mol% and the selectivity to triethylene glycolic acid sodium salt to be 95.0 mol%.

EXAMPLE 5

An autoclave having an inner volume of 500 ml was charged with 83.4 g (0.35 mol) of pentaethylene glycol, 28.0 g (0.7 mol) of sodium hydroxide, 111 g of water and 8.3 g of a catalyst containing copper and zirconium compound which had been obtained by adding to a solution of 18.2 g of zirconium oxynitrate and 8.0 g of copper nitrate in 300 ml of water an aqueous sodium hydroxide solution to cause precipitation of hydroxide, washing the precipitate with water, drying it, heating dry precipitate in air at 500° C. for 3 hours, and subjecting the resultant composite to reduction under a current of hydrogen gas at 230° C. for 6 hours. After the interior of the autoclave had been displaced with hydrogen gas three times, the reaction was continued at a temperature of 190° C. under a pressure of 10 kg/cm$^2$.G until generation of hydrogen ceased. The time required for the reaction was 6 hours after the temperature had reached 190° C. After completion of the reaction, the reaction product was sampled and analyzed. By the analysis, the conversion of pentaethylene glycol was found to be 98.5 mol% and the selectivity to pentaethylene glycolic acid sodium salt to be 93.0 mol%.

EXAMPLE 6

An autoclave having an inner volume of 500 ml was charged with 90.0 g (0.3 mol) of polyethylene glycol having 300 of average molecular weight, 24.0 g (0.60 mol) of sodium hydroxide, 111 g of water and 9.0 g of a catalyst containing copper and zirconium compound which had been obtained by adding to a solution of 18.2 g of zirconium oxynitrate and 8.0 g of copper nitrate in 300 ml of water an aqueous sodium hydroxide solution to cause precipitation of hydroxide, washing the precipitate with water, drying it, heating dry precipitate in air at 500° C. for 3 hours, and subjecting the resultant composite to reduction under a current of hydrogen gas at 230° C. for 6 hours. After the interior of the autoclave had been displaced with hydrogen gas three times, the reaction was continued at a temperature of 200° C. under a pressure of 15 kg/cm$^2$.G until generation of hydrogen ceased. The time required for the reaction was 8 hours after the temperature had reached 200° C. After completion of the reaction, the reaction product was sampled and analyzed. By the analysis, the conversion of polyethylene glycol was found to be 99.0 mol% and the selectivity to oxydicarboxylic acid sodium salt to be 93.0 mol%.

What is claimed is:

1. A method for the manufacture of an oxydicarboxylic acid salt which comprises subjecting to dehydrogenation an polyethylene glycol represented by the formula I:

$$HO-(CH_2CH_2O)_{\overline{n}}H$$

wherein n is 2 to 14, in the presence of the hydroxide of at least one metal selected from the group consisting of alkali metals and alkaline earth metals, water and a catalyst consisting essentially of zirconium and copper compounds in a weight ratio of between 20 and 1 parts by weight of zirconium per 1 part by weight of copper.

2. A method according to claim 1, wherein the amount of said catalyst is 1 to 70% by weight based on the amount of said polyethylene glycol.

3. A method according to claim 1, wherein the amount of said hydoxide is 0.8 to 1.5 equivalent relative to a hydroxy group of said polyethylene glycol.

4. A method according to claim 1, wherein the amount of said water is not less than 10% by weight based on amount of said polyethylene glycol.

5. A method according to claim 1, wherein the amount of said catalyst is 5 to 30% by weight based on the amount of said polyethylene glycol.

6. A method according to claim 5, wherein the amount of said water is 25 to 500% by weight based on the amount of said polyethylene glycol.

7. A method according to claim 1, wherein said hydroxide is an alkali metal hydroxide.

8. A method according to claim 1, wherein said metal hydroxide is at least one member selected from the group consisting of sodium hydroxide and potassium hydroxide.

9. A method according to claim 1, wherein the reaction temperature is not more than 250° C.

10. A method according to claim 9, wherein the reaction temperature is in the range of 120° to 250° C.

11. A method according to claim 1, wherein the reaction pressure is in the range of 0 to 50 kg/cm$^2$.G.

12. A method according to claim 1, wherein said polyethylene glycol is diethylen glycol and said oxydicarboxylic acid salt is oxydiacetic acid salt.

13. A method according to claim 1, wherein said polyethylene glycol is triethylene glycol and said oxidicarboxylic acid salt is triethylene glycolic acid salt.

14. A method according to claim 1, wherein said polyethylene glycol is tetraethylene glycol and said oxidicarboxylic acid salt is tetraethylene glycolic acid salt.

15. A method according to claim 1, wherein said polyethylene glycol is pentaethylene glycol and said oxydicarboxylic acid salt is pentaethylene glycolic acid salt.

16. A method according to claim 1, wherein said polyethylene glycol is polyethylene glycol having 200 to 400 of average molecular weight and said oxydicarboxylic acid salt is a corresponding polyethylene glycolic acid salt.

* * * * *